(12) United States Patent
Castor

(10) Patent No.: US 12,071,419 B2
(45) Date of Patent: Aug. 27, 2024

(54) THERMAL CONVERSION OF CBDA AND OTHER CARBOXYLIC CANNABINOIDS

(71) Applicant: Trevor Percival Castor, Arlington, MA (US)

(72) Inventor: Trevor Percival Castor, Arlington, MA (US)

(73) Assignee: Aphios Corporation

( * ) Notice: Subject to any disclaimer, the term of this patent is extended or adjusted under 35 U.S.C. 154(b) by 86 days.

(21) Appl. No.: 17/727,788

(22) Filed: Apr. 24, 2022

(65) Prior Publication Data

US 2022/0340538 A1 Oct. 27, 2022

Related U.S. Application Data

(60) Provisional application No. 63/179,148, filed on Apr. 23, 2021.

(51) Int. Cl.
| | | |
|---|---|---|
| *C07D 311/80* | (2006.01) | |
| *B01J 3/04* | (2006.01) | |
| *C07C 37/50* | (2006.01) | |
| *C07C 37/74* | (2006.01) | |
| *C07C 39/19* | (2006.01) | |

(52) U.S. Cl.
CPC ............... *C07D 311/80* (2013.01); *B01J 3/04* (2013.01); *C07C 37/50* (2013.01); *C07C 37/74* (2013.01); *C07C 39/19* (2013.01)

(58) Field of Classification Search
CPC .................................................. C07D 311/80
USPC .......................................................... 549/390
See application file for complete search history.

(56) References Cited

U.S. PATENT DOCUMENTS 6,630,507 B1   10/2003   Hampson et al.

OTHER PUBLICATIONS

Compton et al., J. Pharm Experimental Therapeutics (1993) vol. 265(1), pp. 218-226.*

* cited by examiner

*Primary Examiner* — Taofiq A Solola

(57) ABSTRACT

This invention is for improving the manufacturing pharmaceutical grade CBD and other cannabinoids following current Good Manufacturing Practices (cGMP) of the US FDA for use in clinical trials for CNS and other indications by the NIH and other researchers. The major cannabinoids in marijuana (*Cannabis*) and hemp originate from Cannabigerolic Acid (CBGA) present in the biomass of the plant. Plant enzymes that are specific to different strains of biomass converts CBGA to different carboxylic acids of cannabinoids including Cannabidiolic Acid (CBDA) and Δ9-Tetrahydrocannabinolic Acid (Δ9-THCA). These are relatively stable in the growing and fresh-cut plants. These are converted by thermal decarboxylation to Cannabidiol (CBD) and Δ9-Tetrahydrocannabinol (Δ9-THC), carbon dioxide and water. Cannabinoids can be manufactured by first heating the *Cannabis* biomass to convert carboxylic acids prior to extraction and purification. Alternatively, and preferably because of manufacturing cost and product stability, the carboxylic acids can be first extracted and purified. They can be utilized in the carboxylic acid form or stored in a stable manner until converted to cannabinoids for use in medicine. This invention provides an efficient method for their conversion utilizing a high-pressure reactor under inert conditions.

16 Claims, 13 Drawing Sheets

THERMAL CONVERSION OF CBDA AND OTHER CARBOXYLIC CANNABINOIDS

GOVERNMENT SUPPORT

Research leading to this invention was in part funded by the National Institute on Drug Abuse and the National Cancer Institute, National Institutes of Health, Bethesda, MD, USA.

FIELD OF THE INVENTION

This invention relates to methods for converting Cannabidiolic Acid (CBDA) to Cannabidiol(CBD), Δ9-Tetrahydrocannabinolic Acid (Δ9-THCA) to Δ9-Tetrahydrocannabinol (Δ9-THC) and other carboxylic cannabinoids to non-acidic cannabinoids. The methods entail high pressure thermal conversion systems under controlled temperature and pressure.

BACKGROUND OF THE INVENTION

The legitimate use of marijuana for several medical indications has far outpaced the medical and clinical evaluation of marijuana and specific cannabinoids for different medical uses. In 1997, the National Institutes of Health convened an Ad Hoc Expert Panel to discuss current knowledge of the medical uses of *Cannabis*. The report discussed the importance of other cannabinoids and their potential interaction effects upon THC, stating: "Varying proportions of other cannabinoids, mainly cannabidiol (CBD) and cannabinol (CBN), are also present in *Cannabis*, sometimes in quantities that might modify the pharmacology of THC or cause effects of their own. CBD is not psychoactive but has significant anticonvulsant, sedative, and other pharmacological activity likely to interact with THC." The Institute of Medicine (IOM, 1999) concluded that scientific data indicate the potential therapeutic value of cannabinoid drugs, primarily Δ9-THC, for pain relief, control of nausea and vomiting, and appetite stimulation and clinical trials of cannabinoid drugs for symptom management should be conducted.

Medical marijuana is now approved in 36 states and the District of Columbia for several medical conditions such as cachexia, cancer, chronic pain, epilepsy and other disorders characterized by seizures, glaucoma, HIV, AIDS, Multiple Sclerosis, muscle spasticity and nausea. Progress has been made on several fronts on the use of cannabinoids for medical use such as Charlotte's Web (CW) being used for childhood epilepsy through ad hoc development by patient advocacy groups. Sativex® (GW Pharmaceuticals, England), a drug containing equal proportions of Δ9-THC and CBD, was recently approved as a second-line treatment for Multiple Sclerosis (MS) associated spasticity in Canada, New Zealand and 8 European countries.

The FDA has approved Epidiolex® (GW Pharmaceuticals, England), which contains a purified form of the drug substance cannabidiol (CBD) for the treatment of seizures associated with Lennox-Gastaut syndrome or Dravet syndrome in patients 2 years of age and older. The ready availability of pharmaceutical-grade CBD and a standardized CW product, manufactured following cGMP guidelines, will facilitate clinical evaluation by NIH investigators and other researchers for epilepsy, MS and other CNS diseases. The developed process will also be utilized for the manufacturing of Δ9-THC, already in use for cancer pain and nausea and AIDS-related cachexia, and other cannabinoids in development.

The major cannabinoids in marijuana (*Cannabis*) and hemp originate from Cannabigerolic Acid (CBGA) present in the biomass of the plant. Plant enzymes that are specific to different strains of biomass converts CBGA to different carboxylic acids of cannabinoids including Cannabidiolic Acid (CBDA) and Δ9-Tetrahydrocannabinolic Acid (Δ9-THCA). These are relatively stable in the growing and fresh-cut plants. These are converted by thermal decarboxylation to Cannabidiol (CBD) and Δ9-Tetrahydrocannabinol (Δ9-THC), carbon dioxide and water. The nominal active components of marijuana are thus released by smoking, vaporization and baking in cookies.

This invention is for the thermal conversion of CBDA to CBD, Δ9-THCA to Δ9-THC and manufacturing of pharmaceutical-grade CBD, Δ9-THC and other cannabinoids for clinical evaluation by the NIH and other pharmaceutical companies for Multiple Sclerosis and other CNS diseases, and a standardized Charlotte's Web (CW) product for use by medical marijuana dispensaries in Massachusetts and other states for childhood epilepsy.

SUMMARY OF THE INVENTION

Embodiments of the present invention are directed to methods for converting Cannabidiolic Acid (CBDA) to Cannabidiol(CBD), Δ9-Tetrahydrocannabinolic Acid (Δ9-THCA) to Δ9-Tetrahydrocannabinol (Δ9-THC) and other carboxylic cannabinoids to non-acidic cannabinoids. The methods entail high pressure thermal conversion systems under controlled temperature and pressure. These methods employ the use of inert gases such as carbon dioxide, nitrogen and argon.

Preferably the conversion of CBDA to CBD and Δ9-THCA to Δ9-THC is performed at a controlled pressures and temperatures for specific periods of time.

Preferably the conversion of CBDA to CBD and Δ9-THCA to Δ9-THC is performed at a controlled pressures and temperatures in the presence of an inert gas such as carbon dioxide, nitrogen and argon.

Preferably the conversion of CBDA to CBD and Δ9-THCA to Δ9-THC is performed at a controlled pressures and temperatures in solution form.

Preferably the conversion of CBDA to CBD and Δ9-THCA to Δ9-THC is performed at a controlled pressures and temperatures in $CO_2$, an alcohol such as ethanol or methanol or a mixture of $CO_2$ and an alcohol.

These and other features and advantages will be apparent to those skilled in the art upon reading the detailed description and viewing the drawings briefly described below.

DETAILED DESCRIPTION OF PREFERRED EMBODIMENTS

Figure 1:
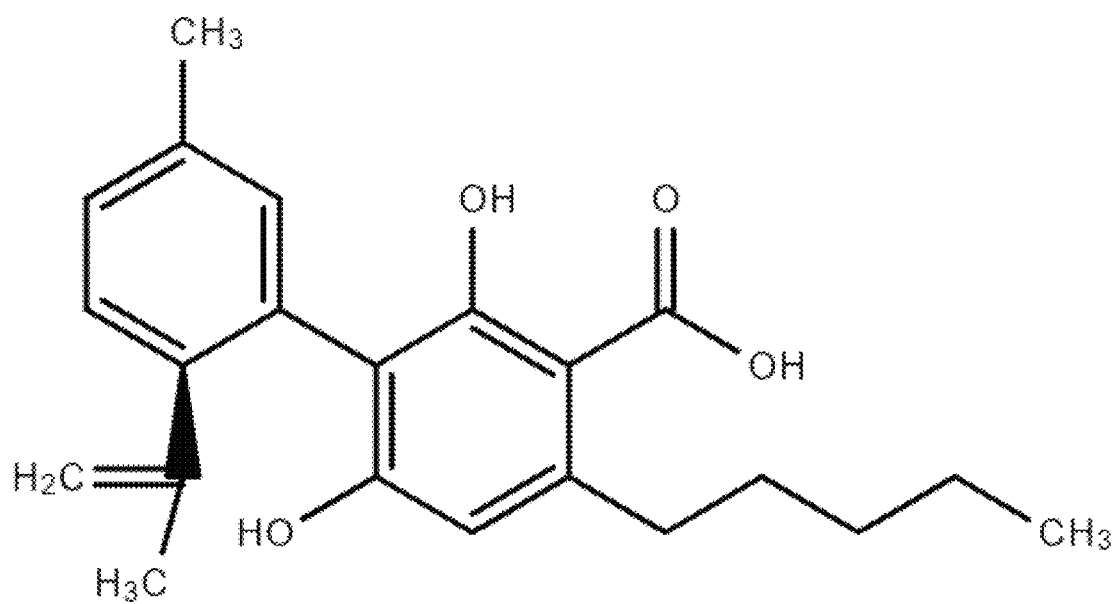
FIG. 1 depicts the chemical structure of Cannabidiolic Acid (CBDA)
Figure 2:
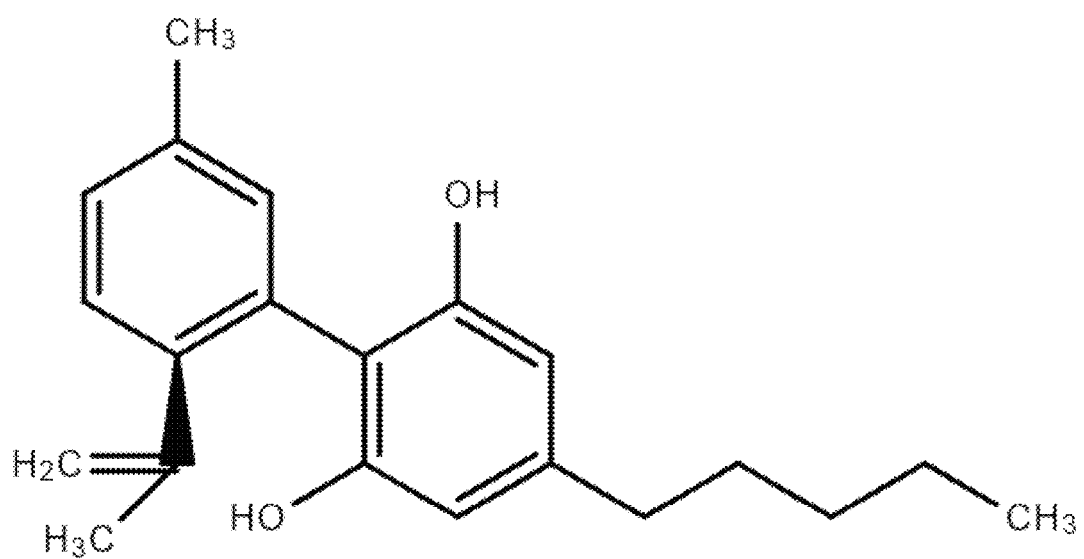
FIG. 2 depicts the chemical structure of Cannabidiol (CBD)
Figure 3:
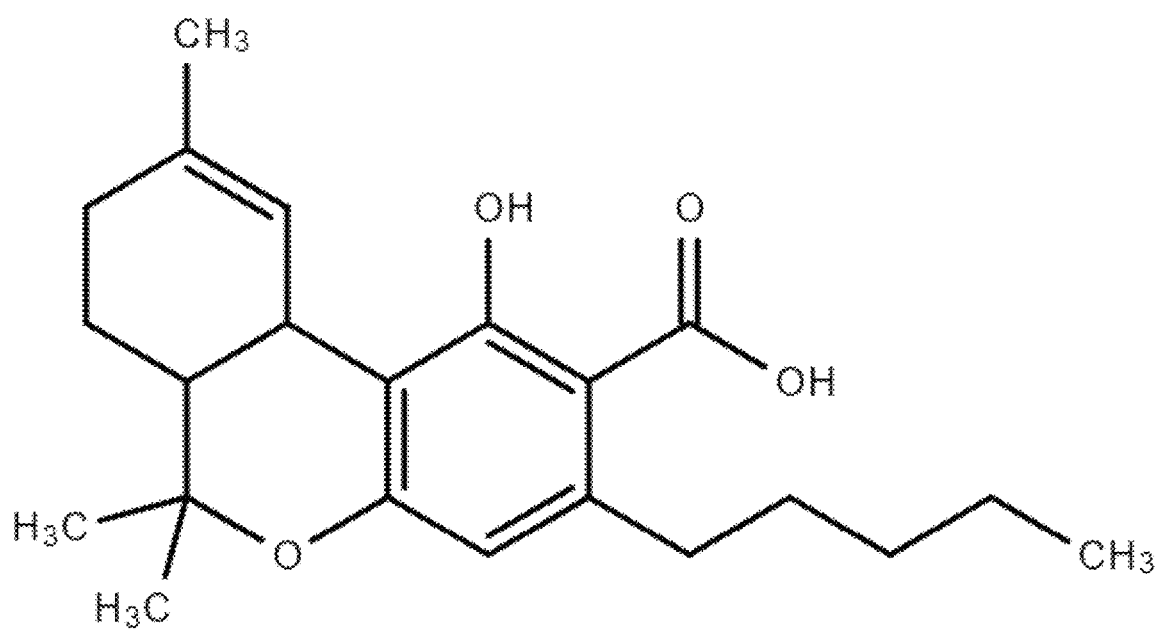
FIG. 3 depicts the chemical structure of Δ9-Tetrahydrocannabinoic Acid (Δ9-THCA)
Figure 4:
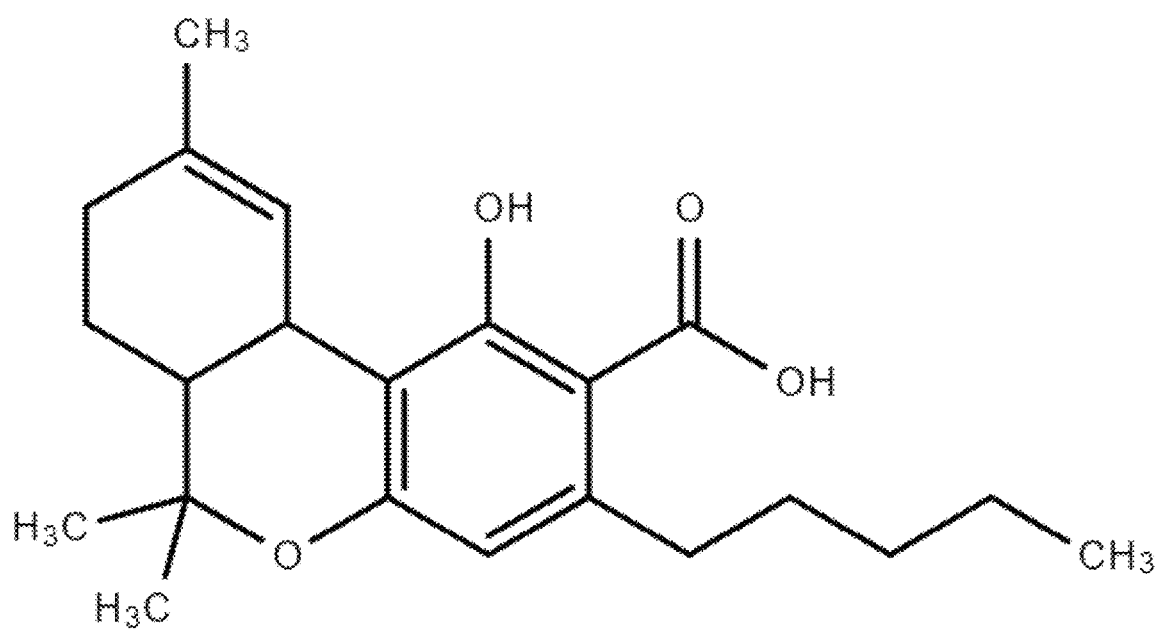
FIG. 4 depicts the chemical structure of Δ9-Tetrahydrocannabinol (Δ9-THC)
Figure 5:
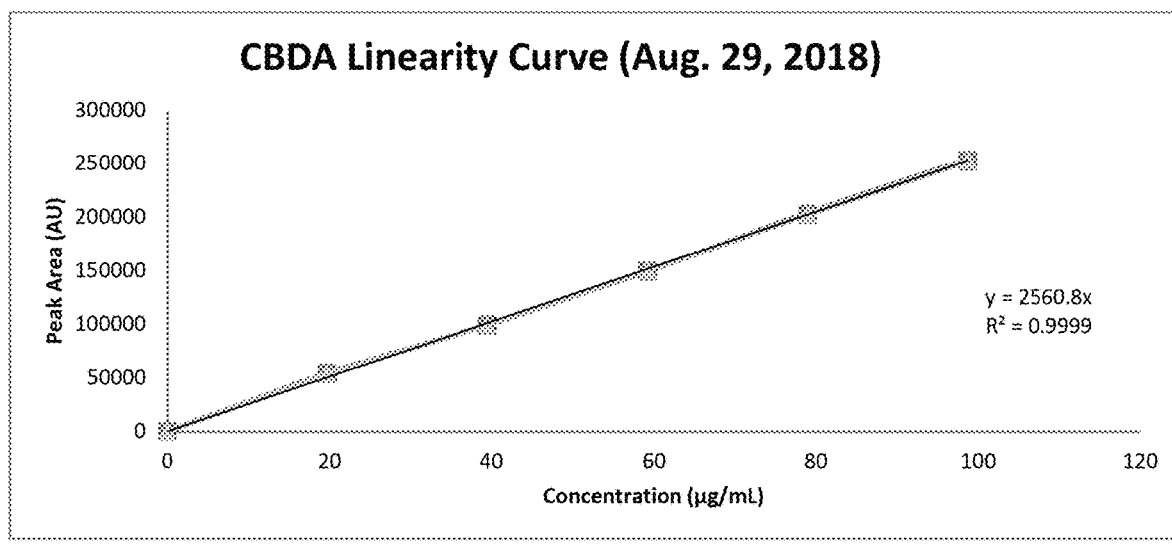
FIG. 5 depicts a Standard Regression Curve for Cannabidiolic Acid (CBDA)
Figure 6:
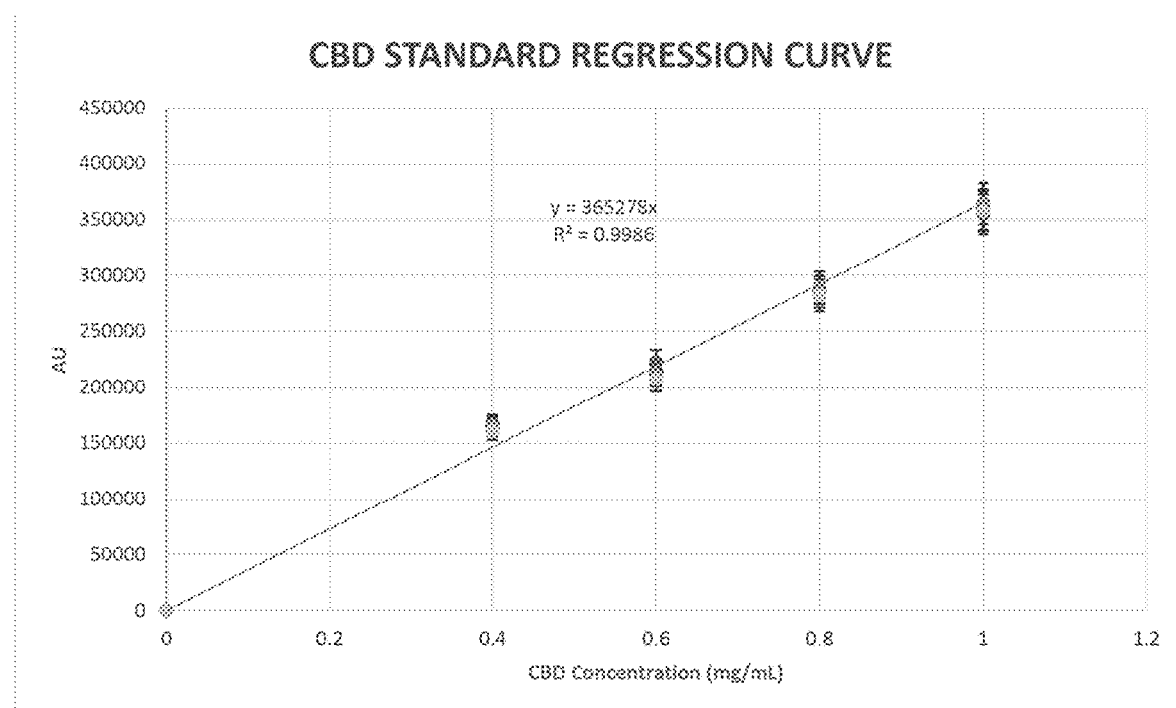
FIG. 6 depicts a Standard Regression Curve for Cannabidiol (CBD)
Figure 7:
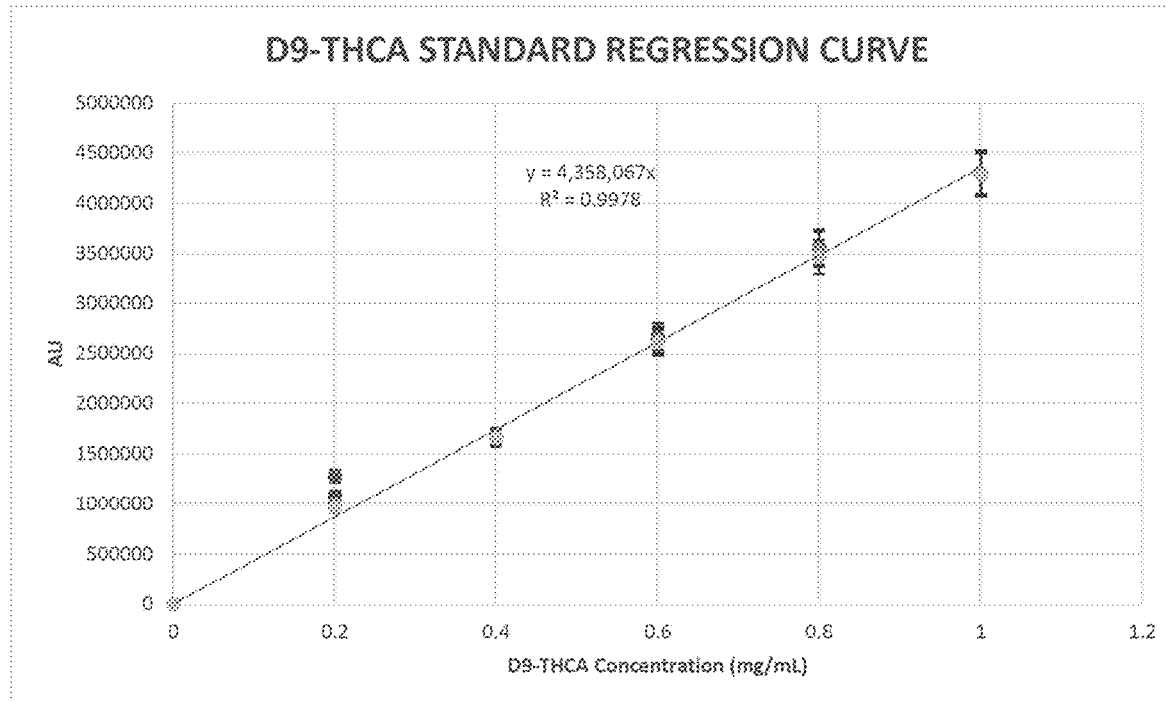
FIG. 7 depicts a Standard Regression Curve for Δ9-Tetrahydrocannabinoic acid (Δ9-THCA)
Figure 8:
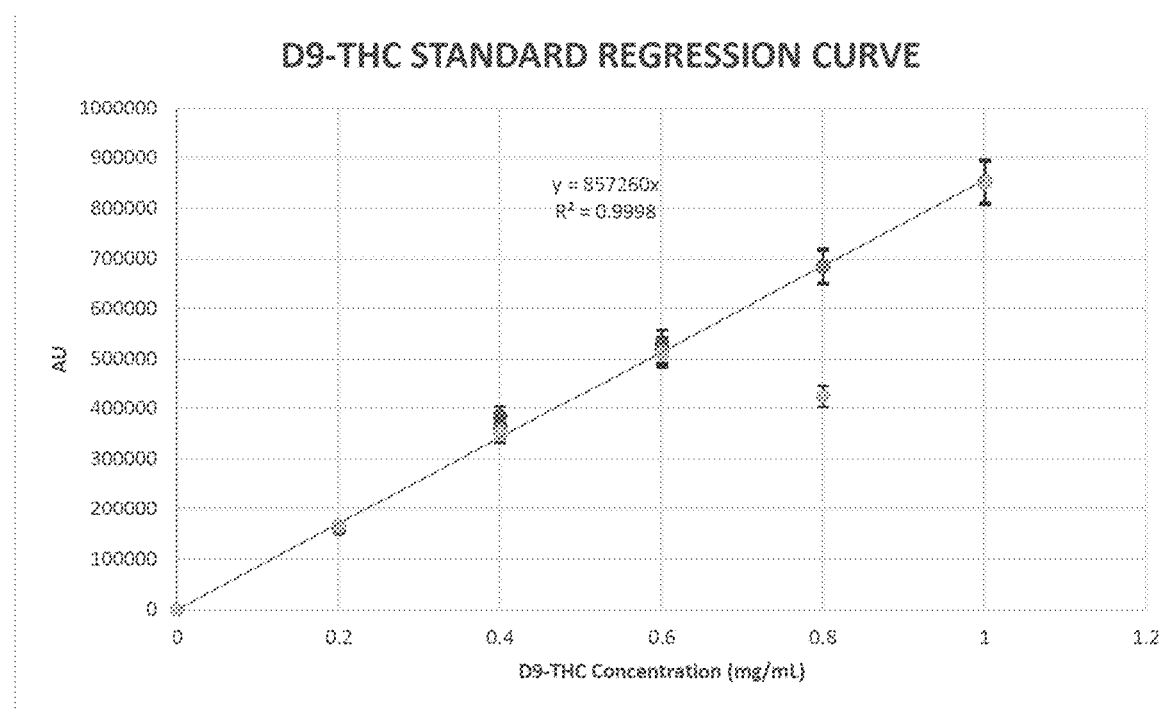
FIG. 8 depicts a Standard Regression Curve for Δ9-Tetrahydrocannabinol (Δ9-THC)
Figure 9:
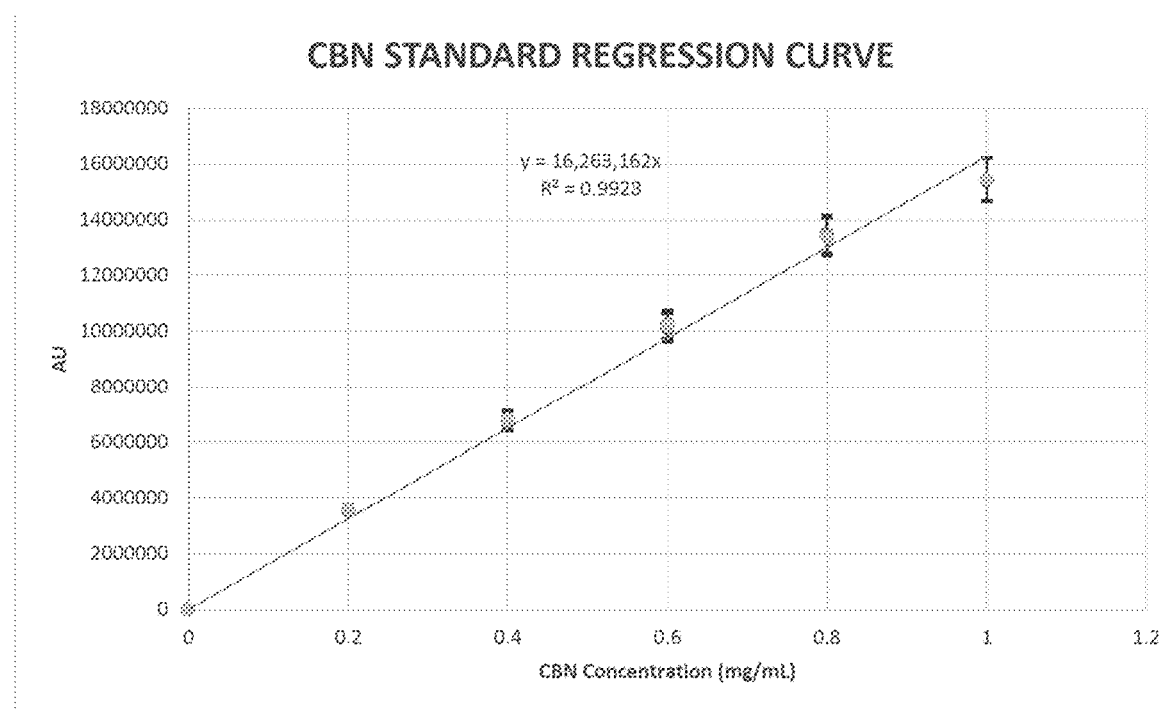
FIG. 9 depicts a Standard Regression Curve for Cannabinol (CBN)

Medical marijuana is now approved in 36 states and the District of Columbia, Guam, Puerto Rico and U.S. Virgin Islands for several medical conditions such as cachexia, cancer, chronic pain, epilepsy and other disorders characterized by seizures, glaucoma, HIV, AIDS, Multiple Sclerosis, muscle spasticity and nausea. Medical marijuana use is on the ballot in additional states, and it is also approved for recreational use in 15 states including Massachusetts, Washington state and California. The legitimate use of marijuana for several medical indications has far outpaced the medical and clinical evaluation of marijuana and specific cannabinoids for different medical uses. In 1997, the National Institutes of Health convened an Ad Hoc Expert Panel to discuss current knowledge of the medical uses of *Cannabis*. The report discussed the importance of other cannabinoids and their potential interaction effects, stating: "Varying proportions of other cannabinoids, mainly cannabidiol (CBD) and cannabinol (CBN), are also present in *Cannabis*, sometimes in quantities that might modify the pharmacology of THC or cause effects of their own. CBD is not psychoactive but has significant anticonvulsant, sedative, and other pharmacological activity likely to interact with THC." The Institute of Medicine (IOM, 1999) concluded that scientific data indicate the potential therapeutic value of cannabinoid drugs, primarily Δ9-THC, for pain relief, control of nausea and vomiting, and appetite stimulation and clinical trials of cannabinoid drugs for symptom management should be conducted. In 2003, NIH was awarded a United States patent for use of cannabinoids as antioxidants and neuroprotectants (Hampson et al., 2003).

Progress has been made on several fronts on the use of cannabinoids for medical use, both through rigorous clinical evaluation of Δ9-THC for cancer pain and nausea and cachexia associated with HIV/AIDS, Δ9-THC/CBD mixtures for Multiple Sclerosis and muscle spasticity, and ad hoc development by localized medical marijuana dispensaries and patient advocacy. The latter is especially true of Charlotte's Web (CW) being used for childhood epilepsy. The strain was named for 5-year-old Charlotte Figi, who had been suffering from a rare disorder called Dravet's syndrome, which caused her to have as many as 300 grand mal seizures a week. Charlotte used a wheelchair, went into repeated cardiac arrest, could barely speak and had flat-lined at least 3 times by 2012. Two years later, Charlotte is largely seizure-free and able to walk, talk and feed herself after taking oil infused with a high CBD *Cannabis* strain with low Δ9-THC content (CBS News, 2014).

Even with lack of well-controlled clinical evidence, families had been migrating to Colorado to seek treatment for their children. Seeds of the high-CBD hemp have migrated to other states. Recently, Utah's Governor signed "Charlee's Law," a hemp supplement bill allowing epilepsy patients access to *cannabis* oils, after six-year-old Charlee Jordan who suffered from Late Infant Batten Disease, a terminal inherited disorder of the nervous system that leads to seizures, and loss of vision and motor skills (The Salt Lake Tribune, 2014). More than 3 million people in North America, 6 million in Europe and 50 million worldwide have epilepsy with highest prevalence for children below five years of age and the elderly with about 30% of patients non-responsive to traditional anti-epileptic drugs (WHO, 2007). The global epilepsy market is expected to reach US$12.9 billion in 2026 from its previous value of US$10.6 billion in 2021 (Visiongain Ltd, 2021). Visiongain further anticipates that the worldwide epilepsy therapeutics market will reach US$16.6 billion in 2031.

Sativex® (GW Pharmaceuticals, England), a drug containing equal proportions of Δ9-THC and CBD, was recently approved as a second-line treatment for Multiple Sclerosis (MS) associated spasticity in Canada, New Zealand and 8 European countries. In October 2013, the Food and Drug Administration approved clinical testing of GW Pharmaceuticals' marijuana-derived drug that is CBD-based. MS is a demyelinating and neurodegenerative disease of the CNS, which is one of the main causes of irreversible neurologic disability in young adults. MS is notoriously heterogeneous in terms of its clinical manifestations and evolution, as well as in terms of its immunopathological substrates. The disease affects 2.5 million people worldwide, of which 400,000 are in the USA and 500,000 in the EU. According to the Cleveland Clinic, MS-related health care costs are thought to be over $10 billion per year in the United States. Despite being the most common human primary demyelinating disease of the CNS, there is no satisfactory treatment as yet for MS, and there is a clear need for the development of agents able to treat this progressive disorder.

The development of a manufacturing process for cannabinoid pharmaceuticals such as CW and CBD are significant because they could be used for studying the physiological effects and the therapeutic value of cannabinoids in humans, potentially leading to new therapeutic agents that could benefit a number of patients. The ready availability of pharmaceutical-grade CBD and a standardized CW product, following cGMP guidelines, will facilitate clinical evaluation by NIH investigators and other researchers for epilepsy, MS and other CNS diseases. The developed process can also be utilized for the manufacturing of Δ9-THC, already in use for cancer pain and nausea and AIDS-related cachexia, and other cannabinoids in development.

Aspects of the present invention employ materials known as supercritical, critical or near-critical fluids. A material becomes a critical fluid at conditions which equal its critical temperature and critical pressure. A material becomes a supercritical fluid at conditions which equal or exceed both its critical temperature and critical pressure. The parameters of critical temperature and critical pressure are intrinsic thermodynamic properties of all sufficiently stable pure compounds and mixtures. Carbon dioxide, for example, becomes a supercritical fluid at conditions which equal or exceed its critical temperature of 31.1° C. and its critical pressure of 72.8 atm (1,070 psig). In the supercritical fluid region, normally gaseous substances such as carbon dioxide become dense phase fluids which have been observed to exhibit greatly enhanced solvating power. At a pressure of 3,000 psig (204 atm) and a temperature of 40° C., carbon dioxide has a density of approximately 0.8 g/cc and behaves much like a nonpolar organic solvent, having a dipole moment of zero Debye.

A supercritical fluid displays a wide spectrum of solvation power as its density is strongly dependent upon temperature and pressure. Temperature changes of tens of degrees or pressure changes by tens of atmospheres can change a compound solubility in a supercritical fluid by an order of magnitude or more. This feature allows for the fine-tuning of solvation power and the fractionation of mixed solutes. The selectivity of nonpolar supercritical fluid solvents can also be enhanced by addition of compounds known as modifiers (also referred to as entrainers or cosolvents). These modifiers are typically somewhat polar organic solvents such as acetone, ethanol, methanol, methylene chloride or ethyl acetate. Varying the proportion of modifier allows wide latitude in the variation of solvent power.

In addition to their unique solubilization characteristics, supercritical fluids possess other physicochemical properties which add to their attractiveness as solvents. They can exhibit liquid-like density yet still retain gas-like properties of high diffusivity and low viscosity. The latter increases mass transfer rates, significantly reducing processing times. Additionally, the ultra-low surface tension of supercritical fluids allows facile penetration into microporous materials, increasing extraction efficiency and overall yields.

A material at conditions that border its supercritical state will have properties that are similar to those of the substance in the supercritical state. These so-called "near-critical" fluids are also useful for the practice of this invention. For the purposes of this invention, a near-critical fluid is defined as a fluid which is (a) at a temperature between its critical temperature ($T_c$) and 75% of its critical temperature and at a pressure at least 75% of its critical pressure, or (b) at a pressure between its critical pressure ($P_c$) and 75% of its critical pressure and at a temperature at least 75% of its critical temperature. In this definition, pressure and temperature are defined on absolute scales, e.g., Kelvin and psia. To simplify the terminology, materials which are utilized under conditions which are supercritical, near-critical or exactly at their critical point with or without small polar concentrations of cosolvents will jointly be referred to as "SuperFluids™" fluids or referred to as "SFS™."

SuperFluids™ [SFS™] can be used for the fractional extraction and manufacturing of highly purified cannabinoids.

Embodiments of the present invention are directed to methods of using supercritical fluids for manufacturing of cannabinoids for use as therapeutics to treat pain, opioid addiction, multiple sclerosis, Parkinson's disease, and nausea and emesis.

Figure 11:
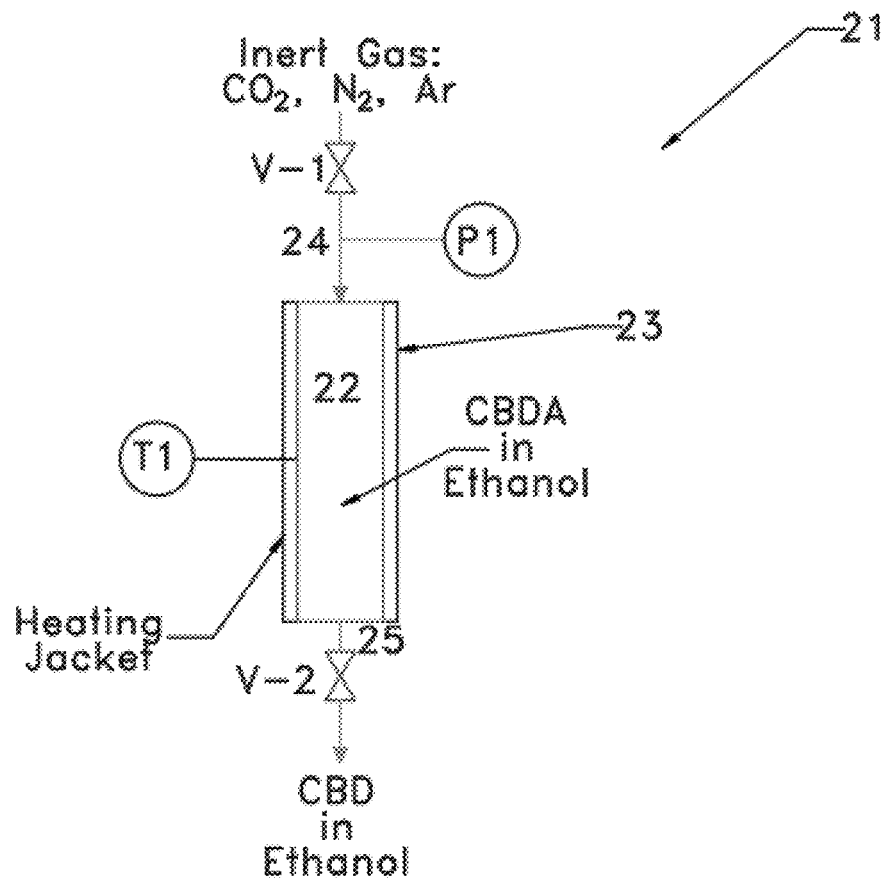
FIG. 11 shows a schematic of a Batch High Pressure Thermal Conversion Unit.

The present method and apparatus will be described with respect to FIG. 11 which depicts in schematic form of the high-pressure thermal conversion apparatus, generally designated by the numeral 21.

The reaction vessel 22 is surrounded by a thermal heating device 23. An inert gas is introduced through line 24 by opening valves V-1 and V-2 on line 25 to purge reaction vessel 22 of air. Valves V-1 and V-2 are then closed. The source of inert gas connected to line 24 is removed and CBDA in solution is connected to line 24. Valve V-1 is opened and a specified amount of CBDA in solution is introduced into the reaction chamber 22 via line 24. Valve V-1 is then closed. CBDA in solution is made up by dissolving CBDA in supercritical, critical, near critical or subcritical $CO_2$ with or without a cosolvent such as ethanol, in 100% ethanol or methanol.

The CBDA in solution is then heated to a specific temperature monitored by T1 and pressure is monitored by P1. After a specific residence time, valve V-2 is opened, and the CBD product is recovered from line 25. This apparatus depicted in FIG. 11 operates in a batch mode.

Figure 12:
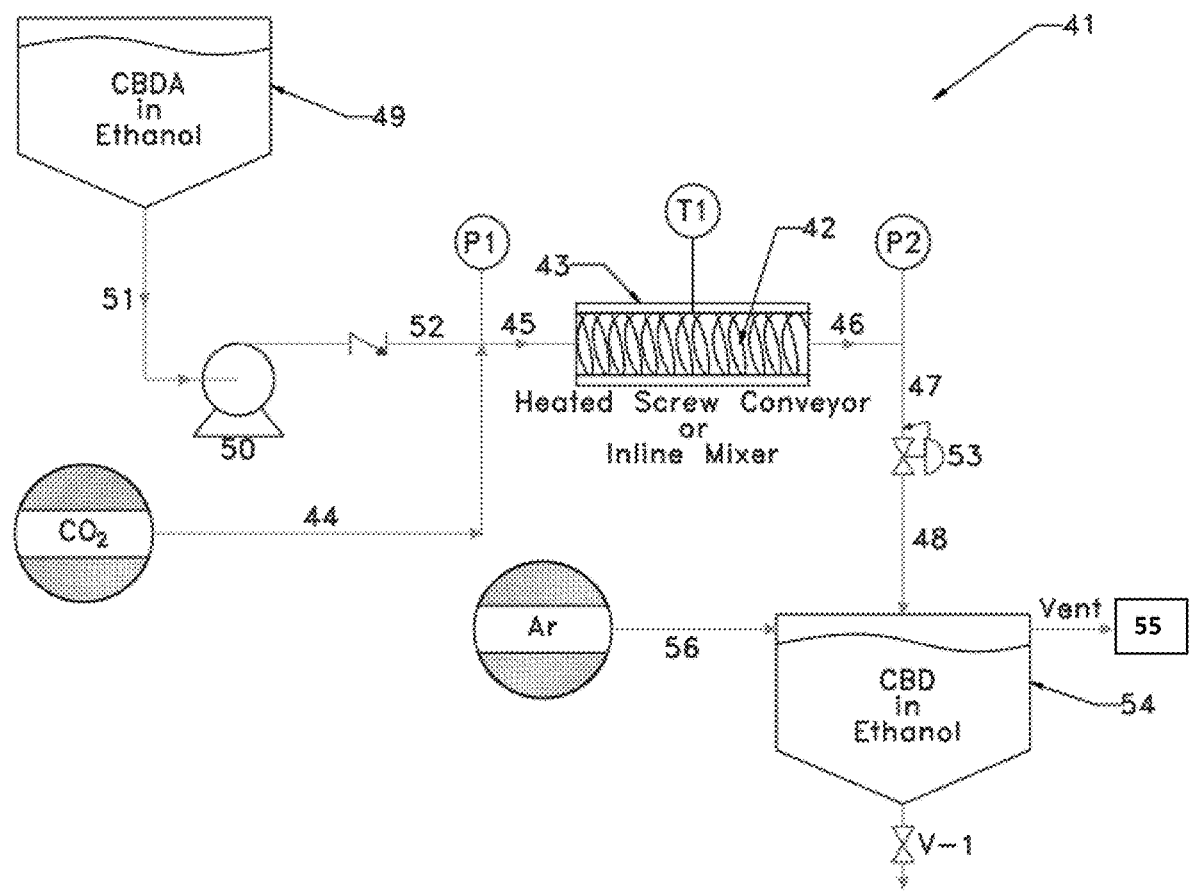
FIG. 12 shows a schematic of a Continuous Flow High Pressure Thermal Conversion Unit.

In another embodiment of the invention, thermal conversion of carboxylic acids of cannabinoids is accomplished in a continuous flow apparatus shown in FIG. 12. FIG. 12 depicts a schematic of a high-pressure thermal conversion apparatus, generally designated by the numeral 41.

The core of the continuous flow apparatus shown in FIG. 12 is a high-pressure reactor 42 that contains a screw conveyor or inline mixer that is surrounded by a heating jacket 43. The apparatus is first purged of air with a source of an inert gas such as $N_2$ flowing through lines 44, 45, 46, 47 and 48. CBDA in solution from supply tank 49 is then introduced to the reactor vessel 22 by pump 50 through lines 51, 52 and 45. CBDA solution is then heated by the jacket surrounding the reactor and/or through heated screw threads in the reactor. Temperature is monitored by T1, and pressure is monitored by P1 and P2.

Product is recovered by flows from the reactor vessel 42 to exit lines 46 and 47. Pressure is reduced in the back-pressure regulator 53 and product exits 53 through line 48 into product collection vessel 54. Excess inert gas is exhausted through vent 55 and replenished by an inert gas such as argon (Ar) via line 56 to provide an inert blanket in the product recovery tank. The CBD product in ethanol or other solvent is recovered from the product tank 54 by opening valve V-1. The process is controlled in terms of flow rate, residence time, pressure and temperature for 99 to 100% conversion of CBDA to CBD without generating any by-products such as CBN in excess of 1%.

The detailed description set forth above is provided to aid those skilled in the art in practicing the present invention. However, the invention described and claimed herein is not limited in scope by the specific embodiments herein disclosed. The embodiments are intended as illustrations of several aspects of the invention. Any equivalent embodiments are intended to be within the scope of this invention. Various modifications of the invention in addition to those shown and described herein will become apparent to those skilled in the art from the foregoing description which do not depart from the spirit or scope of the present inventive discovery. Such modifications are also intended to fall within the scope of the appended claims.

EXAMPLES

Example 1: Cannabiniod Standards, HPLC Analysis And Standard Curves

Cannabinoid Standards: Four (4) standards were purchased for chromatographic assay from Alletch and ChromaDex, Santa Ana, CA They were all purchased at certified concentrations of 1 mg/ml in methanol and transported at ambient atmosphere in sealed glass vials. The standards are as follows:
1. Cannabidiol (CBD), $C_{21}H_{30}O_2$, MW=314.47 g/mol, (99.9%) [Alltech]
2. Δ8-THC, $C_{21}H_{30}O_2$, MW=314.45 g/mol, (90.0%) [Alltech]
3. Cannabinol, $C_{21}H_{26}O_2$ (CBN), MW=310.42 g/mol, (98.9%) [Alltech]
4. Delta-9-Tetrahydrocannabinol (Δ9-THC), $C_{21}H_{30}O_2$, MW=314.45 g/mol, (97%) [ChromaDex, Santa Ana, CA]

Under Aphios' DEA Schedule I license, we requested and obtained 5 ml of 50 mg/ml Δ9-THC in absolute (100%) ethanol for use as an analytical standard in our Phase I SBIR research protocol on Dec. 27, 2002. We also requested and obtained 5 mg of impure Δ9-THCA (Lot No. JMCross 12-6-3) from the University of Mississippi on Apr. 18, 2003. This request was made to use Δ9-THCA as a standard as our research evolved to include the isolation of the carboxylic acid of Δ9-THC.

For this research, we purchased four (4) new standards for chromatographic assay from Restek Corporation, Bellefonte, PA They were all purchased at certified concentrations of 1 mg/ml in methanol and transported on ice in sealed glass vials. The standards are as follows:

5. Cannabidiol (CBD), $C_{21}H_{30}O_2$, MW=314.47 g/mol, (99%) [Restek No. 34011, Lot No. A0103078]
6. Cannabinol (CBN), $C_{21}H_{26}O_2$, MW=310.42 g/mol, (99%) [Restek No. 34010, Lot No. A0106034]
7. Delta-9-Tetrahydrocannabinol (Δ9-THC), $C_{21}H_{30}O_2$, MW=314.47 g/mol, (99%) [Restek No. 34067, Lot No. A0107164]
8. Delta-9-Tetrahydrocannabinolic acid (Δ9-THCA), $C_{22}H_{30}O_4$, MW=358.47 g/mol, (99%) [Restek No. 34093, Lot No. A0106555]

HPLC Analysis: Two (2) HPLC methods were used the analysis of Δ9-THC, Δ-8-THC, CBN, CBD and Δ9-THCA. Since Δ9-THCA is the precursor of Δ9-THC via decarboxylation (heat) and CBN is the degradation (oxidative) product of Δ9-THC, both compounds must be resolved by the chromatography system. CBD is not psychotomimetic in pure form although it does have sedative, analgesic, and antibiotic properties. CBD can contribute to the psychotropic effect by interacting with Δ9-THC to potentiate (enhance) or antagonize (interfere or lessen) certain qualities of this effect. Δ9-THC is the main psychotomimetic (mind-bending) compound of *Cannabis*. Δ-8-THC is slightly less active and is reported in low concentrations, less than 1% of Δ9-THC, and may be an artifact of the extraction/analysis process.

The two HPLC methods used were: (1) a gradient system utilizing a modified Phenomenex method; and (2) an isocratic system that is a modification of the Maripharm, Rotterdam, Netherlands method. The latter system was selected based on peak separation and product purities. This isocratic method utilized a Phenomenex Luna 3 μm C18 column (5 cm×4.6 mm) with a pre-column at 25° C. The mobile phase, at 1.0 ml/min, consisted of 78% methanol: 22% water containing 1% acetic acid. Absorbance was monitored by a Waters Photodiode Array (PDA) detector, Model 996, and measured at 285 nm and 230 nm.

The analytical HPLC system included a Waters 717 Autosampler, 600E System Controller and a Waters Dual-Piston High Pressure HPLC pump, Model No. 600, driven by a Pentium 4 Personal Computer and controlled by a Waters Millennium 4.0 software. Temperature of the HPLC column was controlled by an Eppendorf CH-30 column heater. This isocratic system was utilized to analyze the *Cannabis* biomass and experiments MAJ-1 to MAJ-22. In order to reduce run time for Phenomenex Luna 5 and 10 μm C18 columns, the mobile phase was changed to 80% acetonitrile:20% water containing 0.1% acetic acid at a flowrate or 2.0 ml/min and a column temperature of 30° C. with absorbance measurement at 285 nm. This isocratic system was utilized to analyze fractions from experiments MAJB-1 to MAJB-10. Also, using this isocratic system, a second HPLC system (ISCO) was utilized to monitor the column chromatography utilized in the downstream purification.

A new analytical system was utilized to develop new standard curves and analyze biomass and fractions. The new analytical system consisted of a Waters 2695 Alliance Separations Module with Waters 996 Photodiode Array Detector controlled by Empower Pro software [Aphios' cGMP material code for this equipment is APH-EQ-07120]. The Alliance HPLC system is operated following Aphios' SOP No. EQ-015.

We evaluated a third HPLC method developed by Restek Corporation for their Cannabinoid-specific HPLC column, Raptor ARC-18 (Restek No. 9314A65). The Raptor ARC-18 is a 2.7 μm, 150×4.6 mm column. This HPLC method is a gradient method that included mobile phase A (0.1% formic acid in water) and a mobile phase B (0.1% formic acid in acetonitrile) with the following gradient: 25% A::75% B from 0 to 4.0 min, 0% A:100% B from 4.0 to 4.01 min and 25% A:75% B from 4.01 to 7.0 min. The gradient was run at a combined flowrate of 1.5 mL/min, the column was held at 50° C. and detection was measured at 220 nm.

Utilizing the HPLC method suggested by Restek for analyzing cannabinoids, all of the standards eluted out pretty close to the injection peak, CBD at 1.3 mins, CBD at 1.4 mins, THC at 1.5 mins and THCA at 1.7 mins.

We elected to work with the modified isocratic HPLC method developed by Aphios for C18 columns. We utilized Phenomenex Luna 5 10 μm C18 column, an isocratic mobile phase of 80% acetonitrile::20% water containing 0.1% acetic acid at a flowrate or 2.0 ml/min and a column temperature of 30° C. with absorbance measurement at 285 nm. The standard regressions curves for CBD, Δ9-THC, Δ9-THCA and CBN are respectively shown in FIGS. 5, 6, 7 and 8; three sample sets the dilutions of the standards in methanol were run for each curve.

Example 2: Conversion of CBDA and Δ9-THCA to CBD and Δ9-THC in *Cannabis* Biomass at 120° C.

Ground and oven dried *Cannabis sativa* biomass was separated into 10×0.5 g aliquot portions, which were transferred onto aluminum weigh boats. The 10 weigh boats containing biomass were placed in the oven at 120° C. Ten boats were used in order to perform this experiment in duplicates. Two boats were removed from the oven every 30 minutes, beginning at 60 minutes. The biomass was then allowed to cool to room temperature. Then, using a 250 mL screw top Erlenmeyer flask, the biomass from one boat was added, along with 25 mL of 100% methanol and a magnetic stir bar. The Erlenmeyer flask and its contents were placed in a water bath at 45° C.+/−5° C. on top of a heat/stir plate. The Erlenmeyer flask was then stirred by the magnetic stir bar for 40 minutes. Occasionally, the Erlenmeyer flask had to be removed briefly from the heat/stir plate to recapture the biomass being splattered along the sides of the flask while being stirred.

After 40 minutes, the Erlenmeyer flask was removed from the water bath and filtered through 150 mm filter paper into a 25 mL class A volumetric flask. A splash of methanol was added to the Erlenmeyer flask to create a slurry of the biomass still in the Erlenmeyer flask. The slurry was then dumped into the filter paper to ensure complete extraction. The 25 mL volumetric flask was then adjusted to volume.

Following the filtration, 1.5 mL of extract was transferred into an HPLC vial to be assayed using the isocratic system on the HPLC. Then, a dry weight analysis was completed in triplicates for each extract sample. 2 mL of extract sample was transferred onto aluminum weigh boats and allowed to dry overnight. The following day a weight was obtained and recorded.

A stage zero experiment was then performed in duplicates. Each of the four aliquot portions were undried and unheated. Of the samples weighed out, 2×0.5 g aliquot portions were left unground and 2×0.5 g aliquot portions were ground. From there, using the same warm methanol extraction process listed above, the cannabinoids were extracted and assayed on the HPLC utilizing the isocratic system.

Figure 10:
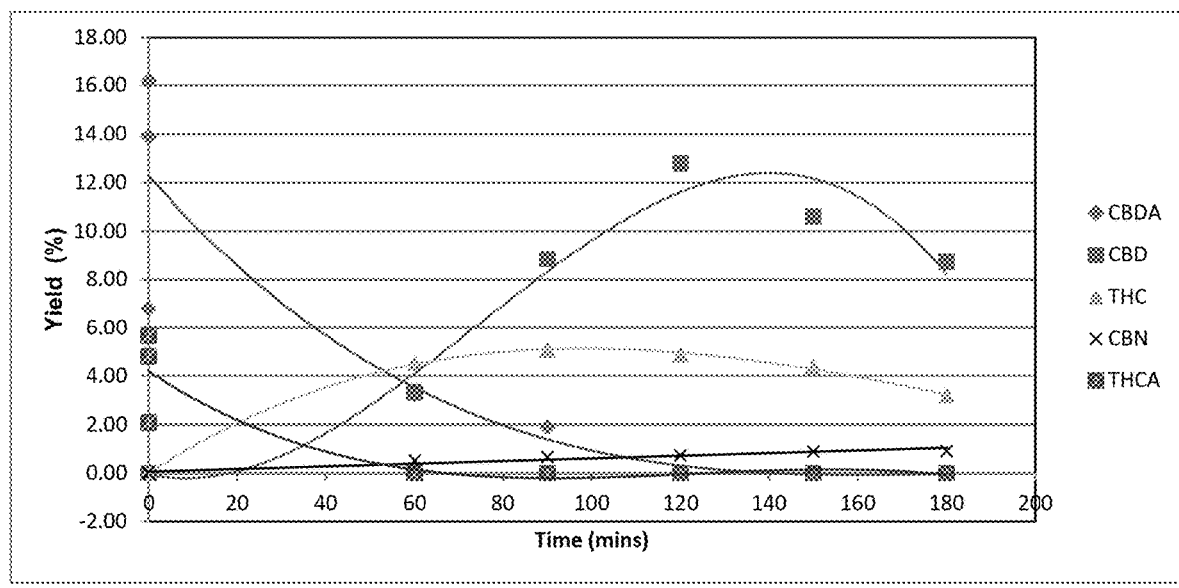
FIG. 10 shows Thermal Conversion of Cannabinoid Carboxylic Acids in *Cannabis Sativa* biomass to Cannabinoids.

The results of this example experiment are shown in FIG. 10. CBDA is present in the *Cannabis* biomass at 60 minutes and at 90 minutes. At 60 minutes CBDA has a percent yield of 3.26% and at 90 minutes a percent yield of 1.89%. However, the *Cannabis* samples at 120 minutes had a 0.00% yield of CBDA. Concomitantly, CBD had a percent yield of 12.78% at 120 minutes. The percent yields of CBDA and CBD over the course of the heated samples are displayed in Table 1.

TABLE 1

CBDA and CBD Percent Yields

| Extract Identification | Heating Time (min) | CBDA Percent Yield | CBD Percent Yield |
| --- | --- | --- | --- |
| 23-01 | 60 | 3.26 | 3.33 |
| 23-02 | 90 | 1.89 | 8.85 |
| 23-03 | 120 | 0.00 | 12.78 |
| 23-04 | 150 | 0.00 | 10.61 |
| 23-05 | 180 | 0.00 | 8.73 |

In Table 2, the absolute purities of CBD and CBDA for the dried, heated and ground samples are listed. At 60 minutes, CBDA has an absolute purity of 33.11% and CBD has an absolute purity of 7.47%. At 120 minutes CBD has an absolute purity of 25.48% and CBDA has an absolute purity of 0.00%.

TABLE 2

Absolute Purities of CBDA and CBD

| Extract Identification | Heating Time (min) | CBDA Absolute Purity (%) | CBD Absolute Purity (%) |
| --- | --- | --- | --- |
| 23-01 | 60 | 33.11 | 7.47 |
| 23-02 | 90 | 19.15 | 17.20 |
| 23-03 | 120 | 0.00 | 25.48 |
| 23-04 | 150 | 0.00 | 24.45 |
| 23-05 | 180 | 0.00 | 21.31 |

Table 3 displays the percent yields for Δ9-THCA and Δ9-THC of the dried, ground and heated samples. At 90 minutes, 23-02 has a percent yield of Δ9-THC of 5.09% and a 0.00% yield for Δ9-THCA.

TABLE 3

Δ9-THCA and Δ9-THC Percent Yields

| Extract Identification | Heating Time (min) | Δ9-THCA Percent Yield | Δ9-THC Percent Yield |
| --- | --- | --- | --- |
| 23-01 | 60 | 0.00 | 4.55 |
| 23-02 | 90 | 0.00 | 5.09 |

TABLE 3-continued

Δ9-THCA and Δ9-THC Percent Yields

| Extract Identification | Heating Time (min) | Δ9-THCA Percent Yield | Δ9-THC Percent Yield |
| --- | --- | --- | --- |
| 23-03 | 120 | 0.00 | 4.90 |
| 23-04 | 150 | 0.00 | 4.38 |
| 23-05 | 180 | 0.00 | 3.20 |

Table 4 displays the absolute purifies for Δ9-THCA and Δ9-THC of the dried, ground and heated samples.

TABLE 4

Absolute purities for Δ9-THCA and Δ9-THC

| Extract Identification | Heating Time (min) | Δ9-THCA Absolute Purity (%) | Δ9-THC Absolute Purity (%) |
| --- | --- | --- | --- |
| 23-01 | 60 | 0.00 | 10.21 |
| 23-02 | 90 | 0.00 | 9.89 |
| 23-03 | 120 | 0.00 | 9.77 |
| 23-04 | 150 | 0.00 | 10.10 |
| 23-05 | 180 | 0.00 | 7.82 |

Table 5 displays the percent yields for the unheated and undried *Cannabis* biomass used as the stage zero experiment. There was no Δ9-THC or CBD present in either the ground or unground *Cannabis* biomass.

TABLE 5

Percent Yield of CBDA and Δ9-THCA for Undried and Unheated *Cannabis*

| Extract Identification | CBDA Percent Yield | Δ9-THCA Percent Yield |
| --- | --- | --- |
| CBD-I-23-UG | 16.18 | 5.67 |
| CBD-I-23-G | 13.89 | 4.82 |

"UG" denotes unground marijuana biomass and "G" denotes ground marijuana biomass.

Table 6 displays the absolute purities of CBDA and Δ9-THCA for the unheated and undried *Cannabis* biomass used as the stage zero experiment.

TABLE 6

Absolute Purities of CBDA and Δ9-THCA for Undried and Unheated *Cannabis*

| Extract Identification | CBDA Absolute Purity (%) | Δ9-THCA Absolute Purity (%) |
| --- | --- | --- |
| CBD-I-23-UG | 164.29 | 13.95 |
| CBD-I-23-G | 140.40 | 10.49 |

"UG" denotes unground marijuana biomass and "G" denotes ground marijuana biomass.

In analyzing the data to determine the optimal heating time at 120° C., it appeared as though 90 minutes was not long enough, as CBDA was still present. At 120 minutes however, there was no CBDA present. At 120 minutes, CBD was present at a percent yield of 12.78%, the highest of all five time periods. Up until then, CBDA was continuing to decarboxylate into CBD. After 120 minutes of heating at 120° C., there was product decomposition and loss. As shown in Table 1, at 150 minutes, CBD had a percent yield of 10.61% and at 180 minutes a percent yield of 8.73%. Heat is needed to convert CBDA into CBD, but exposure to heat at appropriate temperatures for prolonged periods of time will decompose and break down the CBD, resulting in product loss. In accordance with the percent yield, CBD had the highest absolute purity at 120 minutes of heating, resulting in a purity of 25.48%. FIG. 10 graphically displays the percent yield of each cannabinoid throughout the heating process.

Example 3: Conversion of CBDA in Crystalline Form and in Solution Form to CBD

The objective of this experiment was both to convert CBDA to CBD and to determine whether it is more efficacious to do so with CBDA in its crystalline/powder state—dry, or in a solution of methanol or ethanol.

CBD-I-39 sample was used. This sample was CBDA lyophilized powder, confirmed to be 99%+CP (chromatographic purity) and purity was confirmed by LC-MS/MS.

Dry Conversion Test: Placed approximately 10 mg of CBDA from CBD-II-39 in 6 mini glass vials, then placed the vials with caps (off) in the Bel-Art globe. With 1.0 mL mini glass vials inside Bel-Art globe, sealed the Bel-Art globe and flowed nitrogen through the globe for 8 minutes at 10 psig with venting until the globe was purged of air. Once purged, sealed the globe, continued to flow nitrogen in the globe for an additional 3 minutes at 10 psig, and allowed the vials to sit under the nitrogen atmosphere for 10 minutes with nitrogen still flowing. The vials were then capped and the globe was opened.

The vials were placed in the heating block which had been equilibrated to 120° C. One sample, the control, was placed on the counter, away from the heat, sealed and covered in tin foil to prevent heat and light exposure.

Samples were removed at the following intervals: 15 minutes, 30 minutes, 45 minutes, 120 minutes and 270 minutes. At the end of each sample time period, the sample was allowed to cool for 5 minutes and then 1 mL of methanol was added to each sample, vortexed to ensure dissolution of material, and a 100 µL aliquot was removed for HPLC analysis.

Solution Conversion Test: Prepared 5 samples in mini glass vials in the following manner: Weighed out approximately 10 mg of CBD-II-39 CBDA powder into each mini glass vial. To each vial added 1 mL of methanol. Placed all the vials in the Bel-Art globe and the procedure for purging the vials of air was repeated as was performed in the Dry conversion test. The vials were capped, and once removed from the globe, placed in the heat block. Samples were removed, cooled and tested via HPLC at the following time increments: 30 minutes, 45 minutes, 60 minutes, 75 minutes and 90 minutes.

Dry Conversion Results: Utilizing the dry conversion method, conversion of CBDA to CBD was observed as early as 15 minutes, 79.85% CBDA and 20.15% CBD. After approximately 120 minutes (2 hours) the ratios were 96.1% CBD and 3.9% CBDA, with percent area reported as 26.81% CBDA and 73.19% CBD. It was observed after 3 hours, that the CBDA had still not completely been converted to CBD with chromatographic results indicating percent area of 9.35% for CBDA and 90.65% CBD, which translates to 98.9% of the solution being CBD by weight.

Additionally, it should be noted that the dry crystals began to melt and turn brown after 15 minutes at 120° C.

Solution Conversion Results: Utilizing the solution conversion method, conversion of CBDA to CBD appears to have gone to completion in approximately 90 minutes. After that time, as indicated by chromatography, the system had converted to 99.5% CBD while 0.5% CBDA remained. Reported areas were 4.06% CBDA and 93.53% CBD.

From the chromatographic results, it would appear that the most efficient route of conversion from CBDA to CBD would be in solution, either methanol or ethanol. The mode of heating, the use of a block heating device, uses convective heat, the transfer of energy between an object and its environment, due to fluid motion. By this definition it is logical that the heating of the solution CBDA converted to CBD both more quickly and more efficiently than that of the solid.

In summary, CBDA from CBD-II-39 was thermally converted at 120° C. under a nitrogen head in time course experiments in CBD-II-58. The CBDA in solid form was converted to 98.6% CBD in 3 hours, and in solution form (dissolved in methanol) to 99.5% CBD in 90 minutes. These experiments determined that the most efficacious means of converting CBDA to CBD was in solution at a temperature of approximately 122° C. and that the conversion is complete after 90 minutes.

The question as to whether or not to convert the carboxylic acid cannabinoids to their "active forms" has arisen due to the need for the extra step to convert from, for instance, CBDA to CBD. The issue really is the stability of the compound in question. CBDA appears to be very stable when stored at −20° C. and shielded from light. With the ability to convert from the acid form to the active form occurring in approximately 90 minutes in solution, the conversion step is considered facile and efficient. It is recommended that the current protocols in place, which call for the isolation of the carboxylic form of the cannabinoids continue, they are very stable once isolated, and that when the active form is desired, the compound be converted in solution, then shipped in solution.

Example 4: Conversion of CBDA in Solution to CBD in Pressurized Reaction Vessel

The objective of this experiment was to convert CBDA to CBD using a pressurized reaction vessel and ethanol.

CBD-I-39 sample was used. This sample was CBDA lyophilized powder, confirmed to be 99%+CP (chromatographic purity) and purity was confirmed by LC-MS/MS.

Initial experiments were performed to convert CBDA to CBD as documented in the report for experiment CBD-II-58 in Example 3. In this experiment it was determined that the most efficacious means of converting CBDA to CBD was in solution at a temperature of approximately 122° C. and that the conversion would be complete after 90 minutes. The difficulty would be attaining a temperature of 122° C. in a large reaction vessel as the boiling point of ethanol is 78.37° C.

This means that a pressurized reaction vessel was necessary to facilitate the conversion. FIG. 11 shows a schematic of the pressurized reaction vessel. Electrical heating tape was applied to the main body of the reaction vessel and was attached to a rheostat to effectively control the temperature.

Preliminary tests were performed to verify that the internal temperature was within 1.0° C. of the external temperature of the vessel.

Various experiments were performed modifying the volume in which the CBDA was dissolved and the temperature at which it was converted. It was determined that monitoring the temperature was inefficient as there were large fluctuations in the temperature despite the use of the rheostat. It was also determined that mixing/stirring was not occurring in the vessel. To remedy this, careful inversion of the vessel was required to actually test the solution that was in the main body of the reaction vessel.

Final procedure for the conversion of CBDA to CBD in the reaction vessel was achieved in experiment CBD-II-76. In this experiment, pressure, not temperature was monitored as the gauge was a more reliable indicator of the conditions internal to the reaction vessel than a temperature reading on the outside of the reaction vessel. Pressure (vapor pressure) of the vessel was maintained at approximately 200 psi (approximately 185 psig) which would mean that the internal temperature of the vessel and the solution/vapor was approximately 165° C. Calculations were based on the Antoine Equation calculator. The Antoine equation is a class of semi-empirical correlations describing the relation between vapor pressure and temperature for pure components. The Antoine equation is derived from the Clausius-Clapeyron relation.

Prior to removal of the sample for testing, approximately 100 μL, the reaction vessel was gently inverted 4 times, maintaining the pressure gauge upright to prevent solution from invading the pressure gauge itself. During inversion, the system experienced a small reduction in pressure, approximately 20-30 psig.

nal temperature of the vessel and the solution/vapor was approximately 165° C. Complete conversion of CBDA to CBD in absolute ethanol (FIG. 13) occurred after 360 minutes (6 hours).

What is claimed is:

1. A method of for converting Cannabidiolic Acid (CBDA) to Cannabidiol (CBD), Δ9-Tetrahydrocannabinolic Acid (Δ9-THCA) to Δ9-Tetrahydrocannabinol (Δ9-THC) and other carboxylic cannabinoids to non-acidic cannabinoids, the method comprising thermal conversion of a carboxylic acid of a cannabinoid by heating such carboxylic acid of a cannabinoid in a pressurized reaction vessel in an inert atmosphere wherein the carboxylic acid of the cannabinoid is dissolved in solvent selected from CO2, alcohol or a mixture of CO2 and an alcohol, and wherein the pressure in the reaction vessel is greater than the vapor pressure of the solvent at thermal conversion temperature of the carboxylic acid for a specific period of time.

2. The method of claim 1 wherein the carboxylic acid of the cannabinoid is Cannabidiolic Acid (CBDA).

3. The method of claim 1 wherein the carboxylic acid of the cannabinoid is Δ9-Tetrahydrocannabinoic Acid (Δ9-THCA).

4. The method of claim 1 wherein the alcohol is methanol or ethanol.

5. The method of claim 4 wherein the alcohol is methanol.

6. The method of claim 1 wherein the inert atmosphere is CO2, nitrogen or argon.

7. The method of claim 6 wherein the preferred inert atmosphere is argon.

8. The method of claim 1 wherein the reaction vessel is heated over a temperature range of 60° to 150° C.

9. The method of claim 8 wherein the temperature is 120° C.

10. The method of claim 1 wherein the reaction vessel is heated for a period in the range of 30 minutes to 6 hours.

TABLE 7

Percentages of Cannabinoids as a Function of Time (minutes).

| | Percent at t = 0 min | Percent at t = 60 min | Percent at t = 120 min | Percent at t = 180 min | Percent at t = 240 min | Percent at t = 300 min | Percent at t = 360 min |
|---|---|---|---|---|---|---|---|
| CBDA | 100 | 68.75 | 17.38 | 2.42 | 2.3 | 3.4 | 0 |
| CBD | 0 | 31.25 | 82.62 | 97.58 | 97.7 | 96.6 | 100 |

Figure 13:
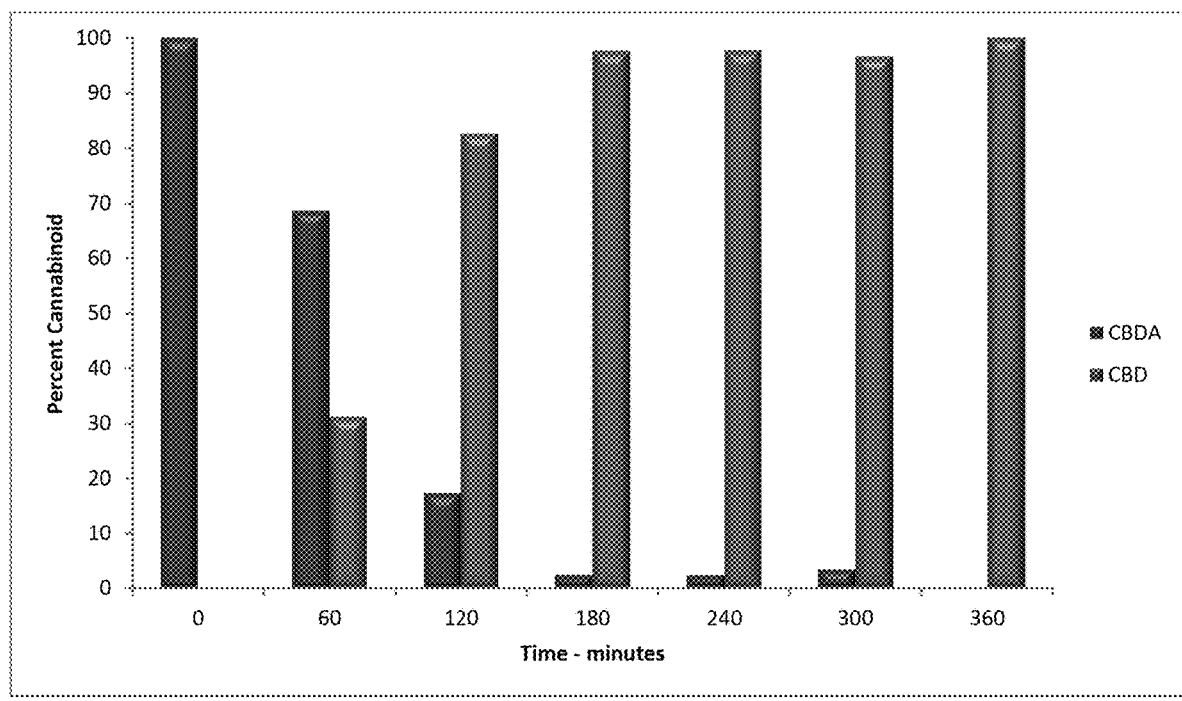
FIG. 13 shows High Pressure Thermal Conversion of Cannabinoid Carboxylic Acids to Cannabinoids.

FIG. 13 shows a graphical representation of the conversion Table 7.

Complete conversion of CBDA to CBD occurred after 360 minutes (6 hours).

In this example, we scaled up conditions from the prior Example 3 for larger amounts and volumes. The challenge in scaling-up is maintaining a temperature of 122° C. in a large reaction vessel as the boiling point of methanol is 64.7° C. and the higher-boiling ethanol alternative is 78.4° C. A pressurized reaction vessel was thus used to facilitate the conversion. Final procedure for the conversion of CBDA to CBD in the reaction vessel was achieved in experiment CBD-II-76.

In summary, pressure, not temperature was monitored as the gauge was a more reliable indicator of the conditions internal to the reaction vessel than a temperature reading on the outside of the reaction vessel. Pressure (vapor pressure) of the vessel was maintained at approximately 200 psi (approximately 185 psig) which would mean that the inter- 11. The method of claim 10 wherein the reaction vessel is heated for at least 6 hours.

12. An apparatus for thermal conversion of a carboxylic acid of a cannabinoid by heating such carboxylic acid of a cannabinoid, comprising a pressurized reaction vessel enclosing an inert atmosphere wherein the carboxylic acid of a cannabinoid is dissolved in solvent selected from CO2, alcohol or a mixture of CO2 and an alcohol, and wherein the pressure in the reaction vessel is greater than the vapor pressure of the solvent at thermal conversion temperature of the carboxylic acid for a specific period of time.

13. The apparatus of claim 12 wherein the carboxylic compound is dissolved in supercritical, near-critical, critical or subcritical carbon dioxide with or without a cosolvent at a temperature in the range of 25 to 60° C. and a pressure in the range of 1,000-5,000 psig.

14. The apparatus of claim 13 where the cosolvent is methanol.

15. The apparatus of claim 13 which operates in a batch mode.

16. The apparatus of claim 13 which operates in a continuous flow mode.

\* \* \* \* \*